(12) United States Patent
Slyusarenko

(10) Patent No.: US 12,393,642 B2
(45) Date of Patent: Aug. 19, 2025

(54) ELECTRONIC DEVICES AND CONTROLLING METHOD OF THE SAME

(71) Applicant: SAMSUNG ELECTRONICS CO., LTD., Suwon-si (KR)

(72) Inventor: Kostyantyn Slyusarenko, Kiev (UA)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 287 days.

(21) Appl. No.: 17/566,412

(22) Filed: Dec. 30, 2021

(65) Prior Publication Data

US 2022/0207298 A1 Jun. 30, 2022

(30) Foreign Application Priority Data

Dec. 30, 2020 (KR) ........................ 10-2020-0187496

(51) Int. Cl.
*G06F 18/214* (2023.01)
*G06N 3/045* (2023.01)
*G06N 3/088* (2023.01)

(52) U.S. Cl.
CPC ........... *G06F 18/214* (2023.01); *G06N 3/045* (2023.01); *G06N 3/088* (2013.01)

(58) Field of Classification Search
CPC ..... G06F 18/214; G06F 18/217; G06N 3/045; G06N 3/088; A61B 5/4806; A61B 5/165; A61B 5/746
See application file for complete search history.

(56) References Cited

U.S. PATENT DOCUMENTS

| | | |
|---|---|---|
| 10,210,036 B2 | 2/2019 | Iyer et al. |
| 2015/0112156 A1 | 4/2015 | He et al. |
| 2015/0199010 A1 | 7/2015 | Coleman et al. |
| 2016/0306935 A1 | 10/2016 | Rajan et al. |
| 2017/0017769 A1 | 1/2017 | Tekumalla et al. |
| 2018/0060757 A1 | 3/2018 | Li et al. |
| 2018/0125418 A1 | 5/2018 | Haakma et al. |
| 2019/0104985 A1 | 4/2019 | Raymann et al. |

(Continued)

FOREIGN PATENT DOCUMENTS

| | | |
|---|---|---|
| CN | 107708528 A | 2/2018 |
| CN | 108882880 A | 11/2018 |

(Continued)

OTHER PUBLICATIONS

Kostyantyn Slyusarenko et al., "Smart alarm on sleep stages prediction", Jul. 2020, pp. 1-4 (4 pages total).

(Continued)

*Primary Examiner* — Vernal U Brown
(74) *Attorney, Agent, or Firm* — Sughrue Mion, PLLC

(57) ABSTRACT

An electronic device includes a sensor configured to acquire a biometric signal of a user; a memory configured to store a measured variable of the user; and a processor configured to: receive biometric data of a plurality of other users and labeling data corresponding to the biometric data of the (Continued)

plurality of other users; predict, using an unsupervised learning model, biometric data of the user based on the biometric signal of the user; predict, using a supervised learning model, a biometric condition of the user based on the predicted biometric data of the user, the biometric data of the plurality of other users, and the labeling data.

18 Claims, 16 Drawing Sheets

(56) References Cited

U.S. PATENT DOCUMENTS

| | | | |
|---|---|---|---|
| 2019/0117144 A1 | 4/2019 | Carraro et al. | |
| 2020/0126533 A1* | 4/2020 | Doyle | G10L 15/063 |
| 2020/0273173 A1* | 8/2020 | Kim | G16H 30/40 |
| 2021/0169417 A1* | 6/2021 | Burton | A61B 5/4857 |
| 2021/0345934 A1* | 11/2021 | Landgraf | A61B 5/0022 |
| 2022/0051039 A1* | 2/2022 | Chowdhury | A61B 5/38 |
| 2023/0080175 A1* | 3/2023 | Lee | A61B 5/318 |
| | | | 705/2 |

FOREIGN PATENT DOCUMENTS

| | | |
|---|---|---|
| CN | 109157211 A | 1/2019 |
| CN | 111449645 A | 7/2020 |
| KR | 10-1880678 B1 | 7/2018 |
| KR | 10-2019-0049430 A | 5/2019 |
| KR | 10-2019-0057592 A | 5/2019 |
| KR | 10-2020-0011818 A | 2/2020 |
| KR | 10-2020-0123610 A | 10/2020 |
| WO | 2018/094098 A2 | 5/2018 |

OTHER PUBLICATIONS

International Search Report issued Apr. 19, 2022 by the International Searching Authority in counterpart International Patent Application No. PCT/KR2021/019674.

Schels et al., "Classification of Emotional States in a Woz Scenario Exploiting Labeled and Unlabeled Bio-physiological Data", 2015 18th International Conference, Austin, TX, USA, Sep. 24-27, 2015, pp. 138-147 (10 pages total).

Xu et al., "Affective States Classification using EEG and Semi-supervised Deep Learning Approaches", 2016 IEEE 18th International Workshop on Multimedia Signal Processing (MMSP), IEEE, Sep. 21, 2016 (6 pages total).

Zhang et al., "Multivariate Time Series Missing Date Imputation Using Recurrent Denoising Autoencoder", 2019 IEEE International Conference on Bioinformatics and Biomedicine (BIBM), IEEE, Nov. 18, 2019, pp. 760-764 (5 pages total).

Caldas et al., "Toward Automatic EEG signal Denoising by Quality Metric Optimization", 2020 International Joint Conference on Neural Networks (IJCNN), IEEE, Jul. 19, 2020 (7 pages total).

Mur et al., "An Unsupervised Method for Artefact Removal in EEG Signals", Sensors, 2019, vol. 19, No. 2302, pp. 1-22 (22 pages total).

Communication issued Apr. 23, 2025 by the Chinese Intellectual Property Office in counterpart Chinese Patent Application No. 202180063768.1.

* cited by examiner

ELECTRONIC DEVICES AND CONTROLLING METHOD OF THE SAME

CROSS-REFERENCE TO RELATED APPLICATION

This application is based on and claims priority under 35 U.S.C. § 119 to Korean Patent Application No. 10-2020-0187496, filed on Dec. 30, 2020 in the Korean Intellectual Property Office, the disclosure of which is incorporated herein by reference.

BACKGROUND

1. Field

Embodiments of the present disclosure relate to predicting physiological characteristics, and in particular to an electronic device which predicts a user's physiological characteristics using learning modeling and an associated electronic device control method.

2. Description of the Related Art

A user's physiological characteristics, can be measured through measurement of a specific value and a latent variable estimated on the basis of the measured variable.

A temperature calculated from a thermistor voltage and a heart rate calculated as a main frequency of an electrocardiogram signal can correspond to a measured variable (observed value) for measuring a physiological characteristic. That is, with respect to the physiological characteristic, a user's biometric data can correspond to the measured variable.

The latent variable (latent value), unlike an observable variable, can be defined as a variable which is not directly measured but is estimated from another variable.

In a model for measuring the physiological characteristic, a biological characteristic can correspond to the latent variable.

A method of estimating a latent variable can be performed through expert human analysis or a mathematical model. A sleep stage determined by expert analysis of a polysomnographic signal, a stress level determined by classifying a user's behavior, and an emotion determined by classifying a user's face can correspond to the latent variable.

This latent variable can be predicted based on a labeled dataset and prediction model learning. That is, data set labeling with latent physiological parameters involves complicated medical diagnosis and manual labeling.

A prediction model based on the collected data has difficulty in collecting labeling data and providing optimized data to each user.

Accordingly, there is a need for modeling that provides a prediction optimized for users without depending on separate data in predicting internal variables.

SUMMARY

Provided is an electronic device which predicts a latent variable and a measured variable using different models to optimized the latent variable for a user, and a method of controlling the same.

According to an aspect of the disclosure, an electronic device may include a sensor configured to acquire a biometric signal of a user; a memory configured to store a measured variable of the user; and a processor configured to: receive biometric data of a plurality of other users and labeling data corresponding to the biometric data of the plurality of other users; predict, using an unsupervised learning model, biometric data of the user based on the biometric signal of the user; predict, using a supervised learning model, a biometric condition of the user based on the predicted biometric data of the user, the biometric data of the plurality of other users, and the labeling data.

The biometric data may be a measured variable; and the biometric condition may be a latent variable.

The unsupervised learning model may use data output by the supervised learning model as feedback to predict the measured variable of the user.

The processor may be further configured to operate the unsupervised learning model independently of the labeling data.

The processor may be further configured to obtain a predicted measured variable of the user, using the supervised learning model, based on the measured variable of the user and the labeling data.

The processor may be further configured to: obtain a predicted measured variable of the user, using the unsupervised learning model, based on the measured variable of the user and learned data, determine a personalized measured variable based on the predicted measured variable of the user and the measured variables of the plurality of other users; and predict the latent variable using the supervised learning model based on the personalized measured variable and the learned data.

The processor may be further configured to obtain the personalized measured variable based on a measured variable of the user corresponding to a first time point and a measured variable of the user corresponding to a second time point.

The processor may be further configured to determine a plurality of user variables for predicting the measured variable of the user and the latent variable of the user based on the measured variables of a predetermined physiological characteristic of the plurality of other users and the labeling data corresponding to the measured variables of the other users.

The electronic device of claim 1, may further include an output interface configured to provide an alarm to the user; and an input interface configured to receive a command of the user. The processor may be further configured to determine an alarm time which outputs the alarm based on the command input by the user, and change an output time of the alarm on based on the predicted biometric condition.

According to another aspect of the disclosure, a method of controlling an electronic device may include acquiring a biometric signal of a user; receiving biometric data of a plurality of other users and labeling data corresponding to the biometric data of the other users; predicting, using an unsupervised learning model, biometric data of the user based on the biometric signal of the user; and predicting, using a supervised training model, a biometric condition of the user based on the predicted biometric data of the user, the biometric data of the plurality of other users, and the labeling data. The biometric data is a measured variable of the user, and the biometric condition is a latent variable of the user.

The predicting of the measured variable may include using data output by the supervised learning model as feedback.

The predicting of the measured variable of the user may include operating the unsupervised learning model independently of the labeling data.

The predicting of the measured variable of the user, using the supervised learning model, may include obtaining a predicted measured variable of the user based on the measured variable of the user and the labeling data.

The predicting of the latent variable of the user, using the unsupervised learning model, may include obtaining a predicted measured variable of the user based on the measured variable of the user and learned data. The method may include obtaining a personalized measured variable based on the predicted measured variable of the user and the measured variables of the plurality of other users. The latency variable of the user may be predicted using the supervised learning model based on the personalized measured variable and the learned data.

The determining the personalized measured variable may include obtaining the personalized measured variable of the user using the unsupervised learning model based on the measured variable of the user corresponding to a first time point and the measured variable of the user corresponding to a second time point.

The method may further include obtaining a plurality of user variables based on measured variables of a predetermined physiological characteristic of the plurality of other users and labeling data corresponding to the measured variables of the other users. Predicting the measured variable of the user and the latent variable of the user may be based on the measured variables of the predetermined physiological characteristic of the plurality of other users and the labeling data corresponding to the measured variables of the other users.

The method may further include determining a time to output an alarm based on a command input by the user; and changing the output time of the alarm on based on the predicted biometric condition.

According to another aspect of the disclosure an electronic device may include an input interface configured to receive an alarm time from a user; an output interface configured to output an alarm to the user; a sensor configured to acquire a biometric signal of the user corresponding to a sleep characteristic, the biometrical signal comprising a photoplethysmogram (PPG) and accelerometer (ACC) data; a memory configured to store the biometric signal of the user corresponding to the sleep characteristic; and a processor configured to: receive labeling data comprising biometric data of the sleep characteristic of a plurality of other users and polysomnography data corresponding to the biometric data of the other users; predict biometric data of the user based on the biometric signal of the user using an unsupervised learning model; predict a sleep condition of the user based on the predicted biometric data of the user, the biometric data of the plurality of other users, and the labeling data.

The processor may be further configured to determine an alarm time output range based on an alarm time input by the user, and change the alarm time in the alarm time output range based on the predicted sleep condition.

The sensor may include at least one of a photoplethysmography device, a gyro sensor, a blood oxygen measurement sensor, an electrocardiogram sensor, a bioimpedance sensor, or a temperature sensor.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1A:
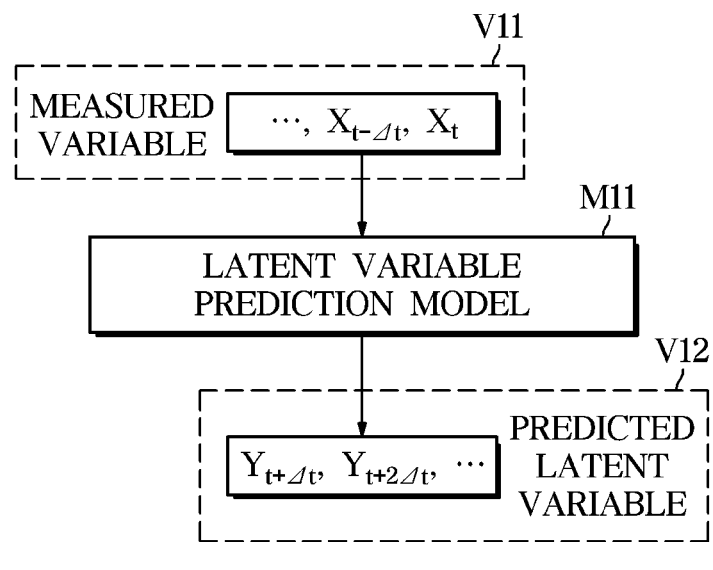
FIG. 1A is a diagram of a prediction model according to an embodiment.

The same reference numerals refer to the same elements throughout the disclosure. The disclosure does not describe all elements of embodiments, and general contents in the technical field including the present disclosure or contents which overlap between the embodiments are omitted. The terms 'part, module, member, or block' used in the disclosure may be implemented as software or hardware, and according to embodiments, a plurality of 'parts, modules, members, or blocks' may be implemented as a single component, or one 'part, module, member, or block' may include a plurality of components.

Throughout the disclosure, a case in which a part is "connected" to another part includes not only direct connection but also indirect connection, and the indirect connection includes connection through a wireless communication network.

Further, a case in which a part "includes" a certain component means that other components may be further included, rather than excluding other components, unless otherwise described.

Throughout the specification, a case in which a member is located "on" another member includes not only a case in which a member comes into contact with another member but also a case in which still another member is present between the two members.

Terms such as first, second, and the like are used to distinguish one component from another component, and the components are not limited by the above-mentioned terms.

In the disclosure, the singular form is intended to also include the plural form unless the context clearly indicates otherwise.

In each step or operation, identification code is used for convenience of description, and the identification code does not describe an order of each step, and each step may be differently performed from the specified order unless the specific order is clearly disclosed in the context.

Hereinafter, the working principle and embodiments will be described with reference to the accompanying drawings.

Figure 1B:
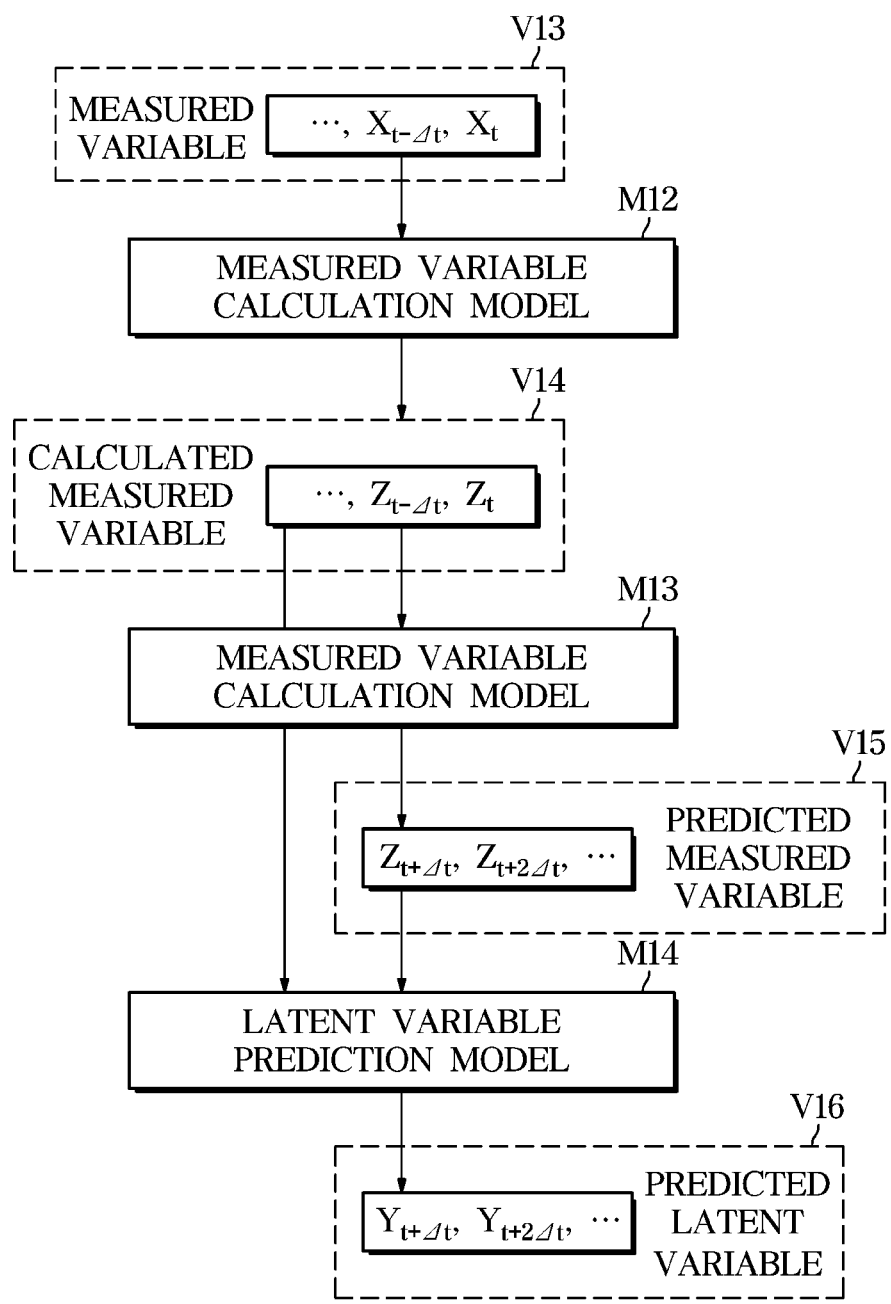
FIG. 1B is a diagram of a prediction model according to another embodiment.

FIG. 1A is a diagram of a model for predicting a latent variable according to an embodiment. FIG. 1B is a diagram of a model for predicting a latent variable according to another embodiment.

Referring to FIG. 1, one latent variable prediction model may be used to predict a latent variable V12 based on a measured variable V11.

The measured variable may refer to biometric data which may be measured from a user, and the latent variable may refer to a biometric condition which may be predicted on the basis of measured data.

However, as shown in FIG. 1B, in a prediction process of this latent variable, rather than a unified model, the prediction may be performed by separating a measured variable prediction model M13 and a latent variable prediction model M14.

A measured variable V13 may refer to a variable directly acquired through measurement of a sensor and calculation of a processor.

Biometric data such as temperature calculated from a thermistor voltage, a heart rate calculated as a main frequency of an electrocardiogram signal, and the like may correspond to a measured variable for measuring a physiological characteristic.

A latent variable V15 may be defined as a variable which is not directly measured but is estimated from other variables.

A user's biometric condition such as a sleep stage determined by expert analysis of a polysomnographic signal, a stress level determined by classifying a user's behavior, an emotion determined by classifying a user's face, or the like may correspond to the latent variable.

Specifically, an electronic device according to an embodiment may acquire the measured variable corresponding to the user's physiological characteristic through a sensor module and calculate the measured variable based on the acquired measured variable (V13).

The electronic device may predict the measured variable from the calculated measured variable (V14). As will be described later, an unsupervised learning model may be applied when predicting the measured variable.

The unsupervised learning model for predicting the measured variable may not demand labeling data corresponding to the user's physiological characteristic.

The labeling data may refer to reference data used for medical diagnosis of measured data measured in a user's specific physiological characteristic.

The electronic device may predict the latent variable at a later time through the latent variable prediction model based on the predicted measured variable (V15).

The supervised learning model may be used to predict the latent variable.

In a supervised prediction model, learning may be performed using the above-described labeling data.

In summary, as shown in FIG. 1, the electronic device may use an unsupervised prediction model to predict the measured variable, and may use the supervised prediction model to predict the latent variable.

Like the above, as a different learning model is used according to each variable, prediction may be performed without the labeling data in predicting the measured variable, and an individualizing operation may be performed based on the predicted measured variable as will be described later.

The operations described in FIG. 1 schematically describe the embodiments, and each operation will be described in detail below.

Figure 2:
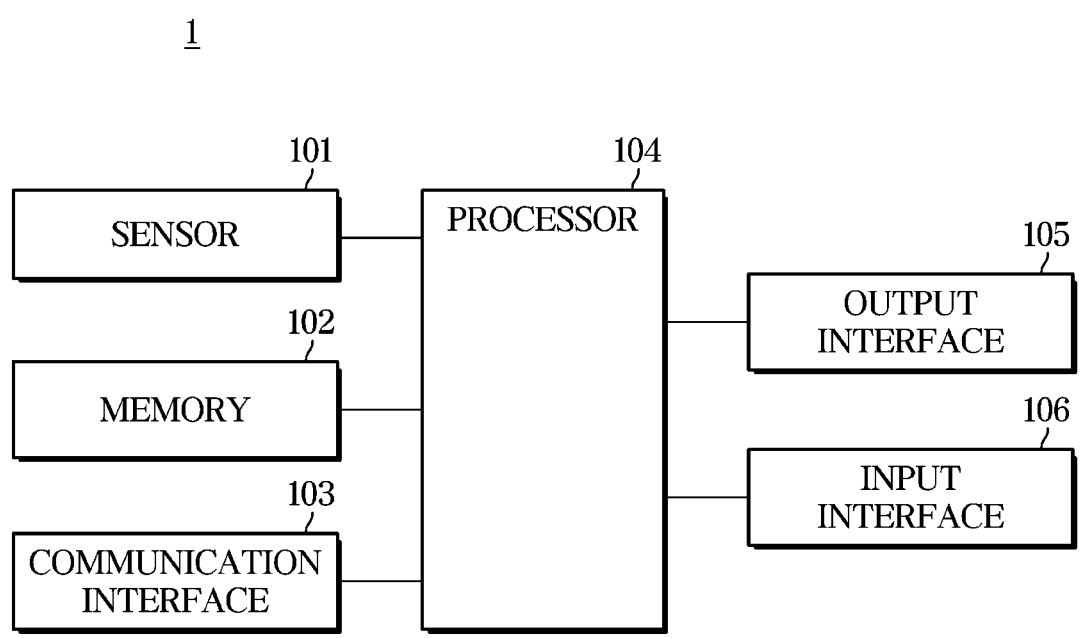
FIG. 2 is a control block diagram of an electronic device according to an embodiment.

FIG. 2 is a control block diagram of an electronic device 1 according to an embodiment.

Referring to FIG. 2, the electronic device 1 according to an embodiment may include a sensor module 101, a communication interface 103, a memory 102, an output interface 105, an input interface 106, and a processor 104 (or multiple processors).

The electronic device 1 may be implemented as a device capable of accessing a server through a network, a computer, or a portable terminal. The computer may include, for example, a notebook computer equipped with a web browser, a desktop computer, a laptop computer, a tablet personal computer (PC), a slate PC, and the like, and the portable terminal is a wireless communication device whose portability and mobility are guaranteed, and may include, for example, all handheld-based wireless communication devices such as a personal communication system (PCS) terminal, a global system for mobile communications (GSM) terminal, a personal digital cellular (PDC) terminal, a personal handyphone system (PHS) terminal, a personal digital assistant (PDA), an international mobile (IMT)-2000 terminal, a code division multiple access (CDMA)-2000 terminal, a W-code division multiple access (W-CDMA) terminal, a wireless broadband internet (WIBRO) terminal, a smart phone (SMART PHONE), and the like and a wearable device such as a watch, a ring, a bracelet, an anklet, a necklace, glasses, a contact lens, a head-mounted device (HMD), or the like.

The input interface 106 may receive a command of a user.

An inputter of the input interface 106 may include hardware devices such as various buttons or switches, a pedal, a keyboard, a mouse, a track-ball, various levers, a handle, a stick, of the like for input of the user.

Further, the input interface 106 may include a device which is a graphical user interface (GUI), that is, software, such as a touch pad or the like for user input. The touch pad may be implemented as a touch screen panel (TSP) to form a layer structure with a display.

The display may also be used as an inputter when configured as a touch screen panel (TSP) forming a layer structure with a touch pad.

The output interface 105 may be a cathode ray tube (CRT) panel, a digital light processing (DLP) panel, a plasma display panel, a liquid crystal display (LCD) panel, an electroluminescence (EL) panel, an electrophoretic display (EPD) panel, an electrochromic display (ECD) panel, a light emitting diode (LED) panel, an organic light emitting diode (OLED) panel, or the like, but is not limited thereto.

Further, the output interface 105 may be a speaker configured to output a sound to the user or a vibration module configured to transmit vibrations, and is not limited in the configuration as long as it is configured to output an alarm to the user.

Other than the above-described devices, as long as the electronic device 1 is a device capable of performing communication, there is no limitation on the device.

The sensor 101 may acquire the measured variable of the user. The measured variable of the user may refer to a biometric signal corresponding to a predetermined physiological characteristic, as will be described later.

The sensor 101 may include a photoplethysmography device, an accelerometer, a gyro sensor, a blood oxygen meter, an electrocardiogram sensor, a bioimpedance sensor, a temperature sensor, and the like, and there is no limitation on the type of configuration capable of acquiring a biometric signal of the user.

The communication interface 103 may receive the measured variables of a predetermined physiological characteristic of a plurality of other users and labeling data corresponding to the measured variables of the other users.

The measured variables of other users may refer to measured variables of users other than a user currently performing prediction of the latent variable.

The labeling data may refer to reference data which serves as a reference in determination of a user's biological characteristic on the basis of the user's measured variable.

Further, this labeling data may refer to data oriented in performing supervised learning, as will be described later.

The communication interface 103 may include one or more components configured to enable communication with an external device, for example, may be provided to include at least one of a short-range communication module, a wired communication module, and a wireless communication module, and may receive the measured variables of other users and the labeling data corresponding to the measured variables of other users from the external device.

The memory 102 may be provided in a configuration for storing the measured variable of the user acquired by the above-described sensor module.

The memory may be implemented as at least one of non-volatile memory devices such as a cache, a read only memory (ROM), a programmable ROM (PROM), an erasable programmable ROM (EPROM), an electrically erasable programmable ROM (EEPROM), and a flash memory, a volatile memory device such as a random-access memory (RAM), or storage media such as a hard disk drive (HDD) and a CD-ROM, but is not limited thereto. A storage may be a memory implemented as a chip separate from the above-described processor with respect to a controller, or may be implemented as a single chip with the processor.

The processor 104 may predict the latent variable corresponding to the predetermined physiological characteristic of the user based on the measured variable of the user.

The predetermined physiological characteristic may refer to a characteristic corresponding to a sleep stage, apnea, a respiratory cycle, a circadian rhythm, stress, alertness, drowsiness, cardiac arrhythmia, or the like, but is not limited to.

The processor may perform unsupervised learning using the user measured variable to predict the user measured variable on the basis of the learned data.

The unsupervised learning is a type of machine learning, and may refer to an operation of finding out how data is configured. In the unsupervised learning, no target is given for an input value.

The processor may predict the latent variable of the user based on the learned data by performing supervised learning based on the predicted user measured variable, the measured variables of the plurality of other users, and the labeling data.

The supervised learning is one method of machine learning for inferring a function from training data. The training data generally may include properties of an input object in the form of a vector, and the desired result for each vector may be included.

The processor 104 (or multiple processors) may predict the user measured variable using supervised learning data as feedback of unsupervised learning data.

That is, the processor 104 may use the supervised learning to predict the measured variable and uses the unsupervised learning to predict the latent variable, and even when separate modeling is formed, mutual data may be used as feedback data.

The processor 104 may perform the unsupervised learning independently of the labeling data. That is, the processor may perform the unsupervised learning in predicting the measured variable. In performing the unsupervised learning, the measured variable may be predicted by performing learning without the reference data with only the measured variable of the user without using the labeling data.

The processor 104 may perform the unsupervised learning using the user measured variable to predict a user measured variable on the basis of the learned data, and may perform the unsupervised learning based on the predicted user measured variable and the plurality of other user measured variables to determine a personalized measured variable corresponding to the user.

That is, based on the measured variable predicted before predicting the latent variable, a personalized measured variable optimized for determining a physiological characteristic for the user by comparing the predicted measured variable with data of other users may be determined.

Hereinafter, the processor 104 may predict the latent variable of the user based on the learned data by performing the supervised learning on the basis of the personalized measured variable.

In determining the personalized measured variable, the processor 104 may perform the unsupervised learning based on a measured variable of the user corresponding to a first time point and a measured variable of the user corresponding to a second time point to determine the personalized measured variable.

The first time point and the second time point may refer to arbitrary time points at which the electronic device acquires data.

The processor 104 may perform the supervised learning based on the measured variables of the predetermined physiological characteristic of the plurality of other users and the labeling data corresponding to the measured variables of the other users to determine a plurality of user variables used to predict the user measured variable and the user latent variable.

The predetermined physiological characteristic refers to a biometric characteristic of the user, and according to one embodiment, an electrocardiogram, a sleep condition, and the like may correspond to the physiological characteristic.

That is, the processor 104 may perform the supervised learning based on the measured variables of other users and the labeling data corresponding to the measured variables of the other users to smoothly predict the measured variable and the latent variable.

The processor 104 may also determine the plurality of user variables in the performed supervised learning. The processor may predict a more personalized latent variable using these determined user variables for prediction of the latent variable.

The processor 104 may be implemented as a memory configured to store data for an algorithm for controlling the operation of components in the electronic device 1 or a program configured to reproduce the algorithm, and a processor configured to perform the above-described operation using the data stored in the memory. In this case, the memory and the processor may be implemented as separate chips. Alternatively, the memory and the processor may be implemented as a single chip.

At least one component may be added or removed according to performance of the components of the electronic device 1 shown in FIG. 2. Further, mutual positions of the components may be changed corresponding to the performance or structure of the system.

Each component shown in FIG. 2 may refer to software and/or hardware components such as a field programmable gate array (FPGA) and an application specific integrated circuit (ASIC).

Figure 3:
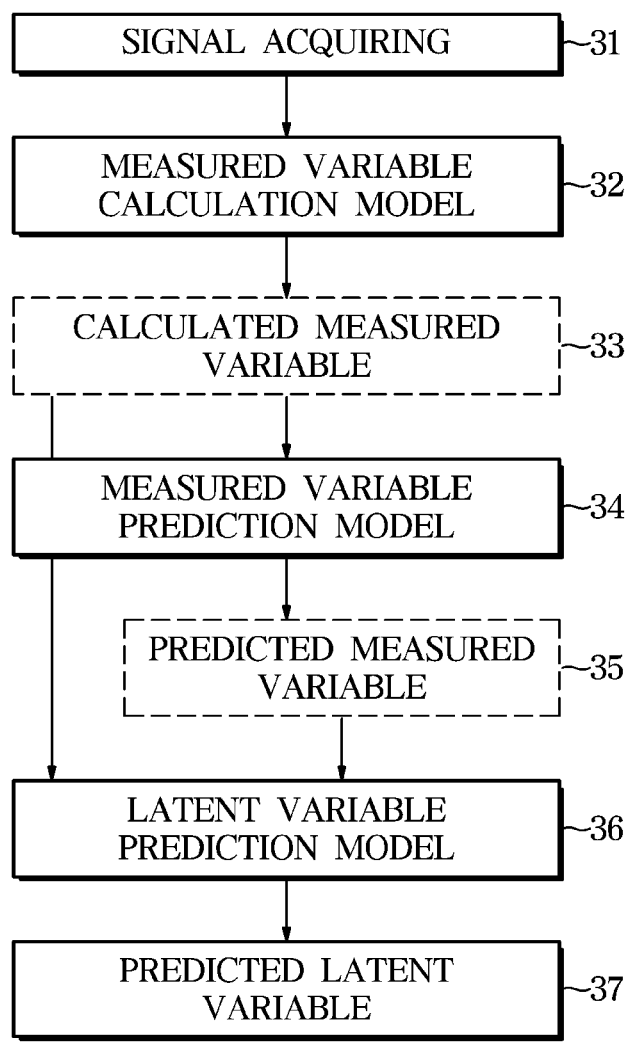
FIG. 3 is a flow chart of a process of predicting the latent variable through a measured variable according to an embodiment.
Figure 4A:
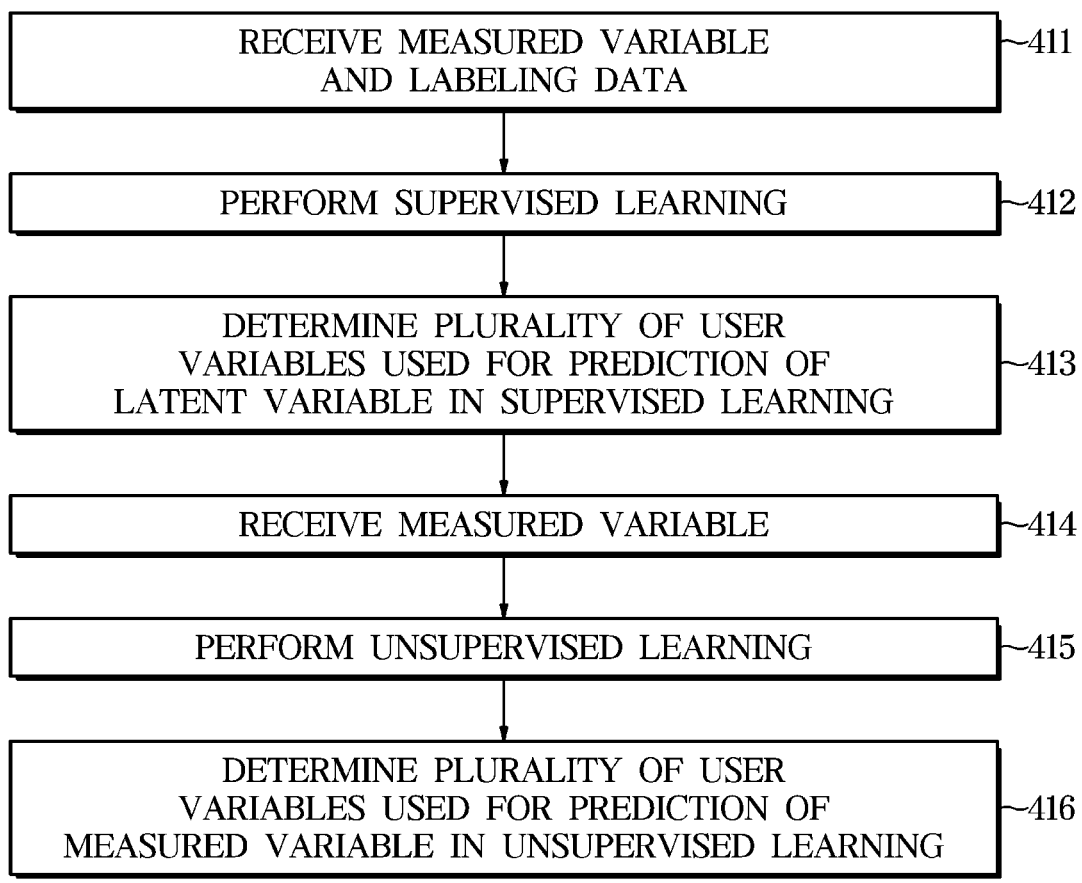
FIG. 4A is a flowchart of a process of an unsupervised learning model for learning the measured variable and a supervised learning model for learning the latent variable according to an embodiment.
Figure 4B:
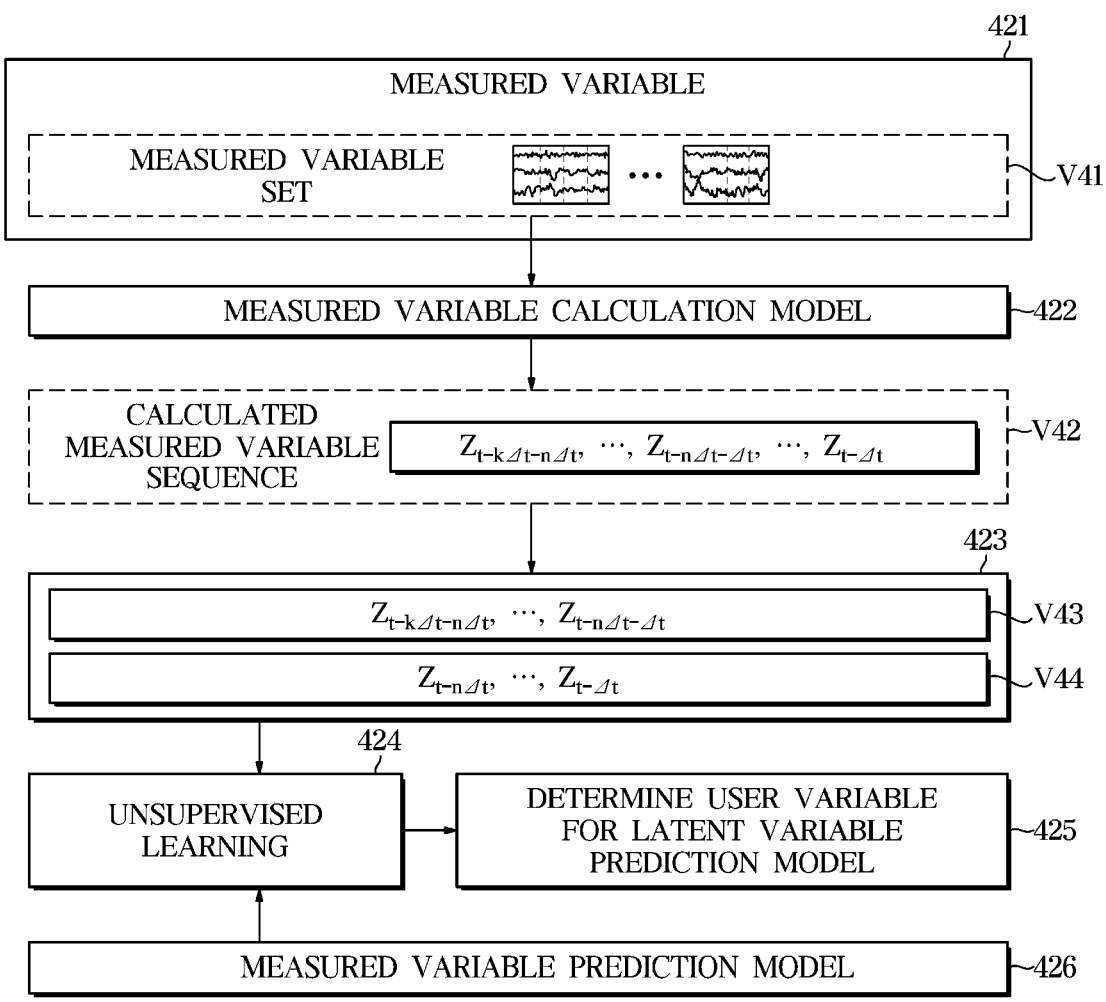
FIG. 4B is a diagram for describing the unsupervised learning model for predicting the measured variable according to an embodiment.
Figure 4C:
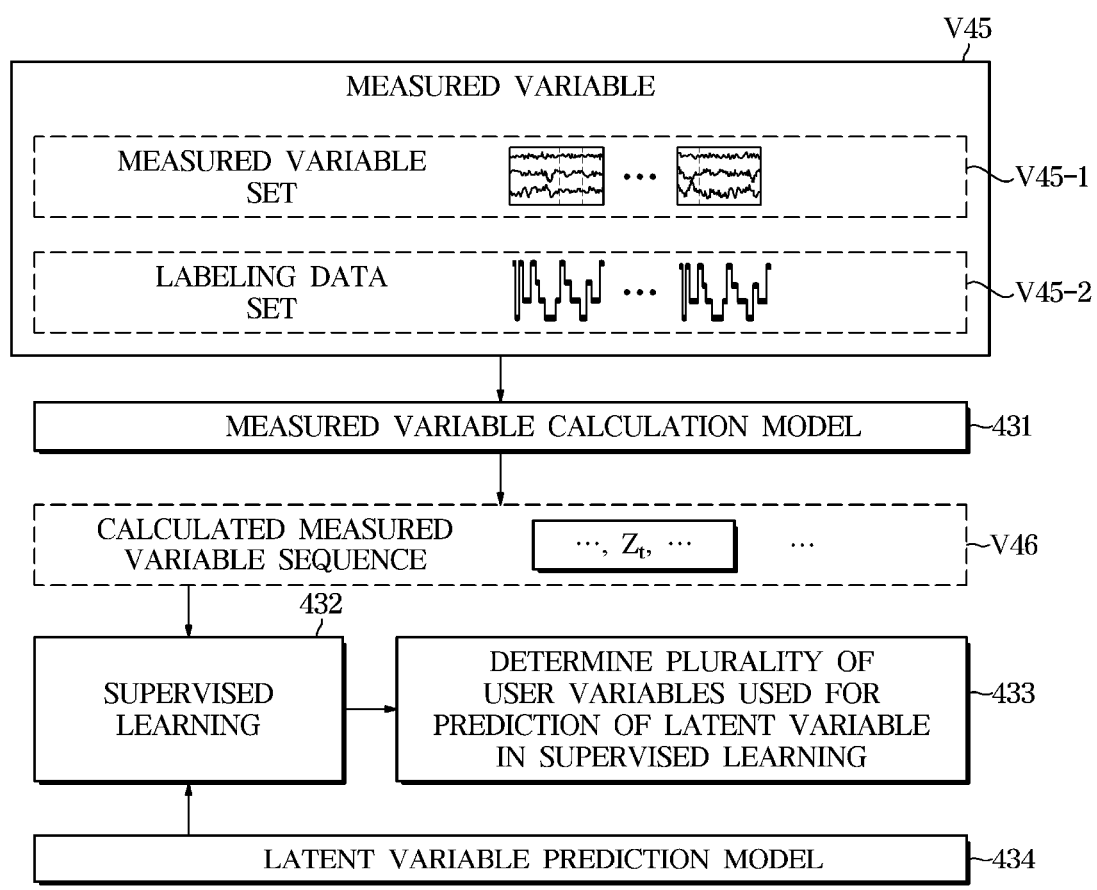
FIG. 4C is a diagram for describing the supervised learning model for predicting the measured variable and the latent variable according to an embodiment.

FIG. 3 is a flow chart of an operation of predicting the latent variable through the measured variable according to an embodiment, FIG. 4A is a flowchart of operations of of the unsupervised learning model for learning the measured variable and the supervised learning model for learning the latent variable according to an embodiment, FIG. 4B is a flowchart of operations of the unsupervised learning model for predicting the measured variable according to an embodiment, and FIG. 4C is flowchart of operations of the supervised learning model for predicting the measured variable and the latent variable according to an embodiment.

Referring to FIGS. 3 and 4A, the processor may perform learning based on the measured variable and the labeling data (411).

The processor may perform the supervised learning based on the labeling data (412). The processor may determine the user variable used for prediction of the latent variable using a value derived as a result of performing the learning in this way (413).

The processor which received the measured variable may perform the unsupervised learning (414 and 415).

As a result of performing the unsupervised learning, the plurality of user variables used for prediction of the measured variable may be determined (416).

Through this learning method, the processor may separate and predict the variable used to predict the measured variable and the variable used to predict the latent variable.

Referring to FIGS. 3 and 4B, FIG. 4B is a flowchart showing the unsupervised learning performed by the processor in more detail according to an embodiment.

Specifically, the electronic device may receive a measured variable V41 through the communication module and the sensor module (421).

The processor may calculate the measured variable on the basis of the received measured variable (422).

Since the measured variable corresponding to a specific physiological characteristic may be measured over time, the processor may determine the measured variable according to a time series. Accordingly, the processor may calculate a measured variable sequence V42.

The processor may separate the measured sequence acquired in the time series into an input measured variable V43 and a reference measured variable V44.

The processor may perform the unsupervised learning using the separated variables (424). The unsupervised learning performed in this way may receive feedback from the measured variable prediction model (426), and may be used as an independent variable in the model for predicting the latent variable (425).

Referring to FIGS. 3 and 4C, FIG. 4C is a view showing the unsupervised learning performed by the processor in more detail according to an embodiment.

The processor may receive a data set V45. The data set may include a measured variable set V45-1 and a labeling data set V45-2 corresponding to the measured variable.

The processor may calculate the measured variable based on the data set (431).

The processor may determine the measured variable sequence based on of this operation (V46).

Unlike FIG. 4B, FIG. 4C may determine the reference variable as the labeling data and perform the supervised learning.

That is, the learning is performed by separating the measured variable into the input value and the reference data in FIG. 4B in which the unsupervised learning is performed, but the supervised learning may be performed using the labeling data as the reference data in FIG. 4C in which the supervised learning is performed (432).

The processor may perform the supervised learning based on this operation, may determine the plurality of user variables used for the prediction of the latent variable (433), and may receive the feedback from the latent variable prediction model (434).

The operations described in FIGS. 3, 4A, 4B, and 4C are for the supervised learning and the unsupervised learning, and there are no limitations on variables used by the processor in performing the supervised learning and the unsupervised learning and models for receiving feedback.

Figure 5A:
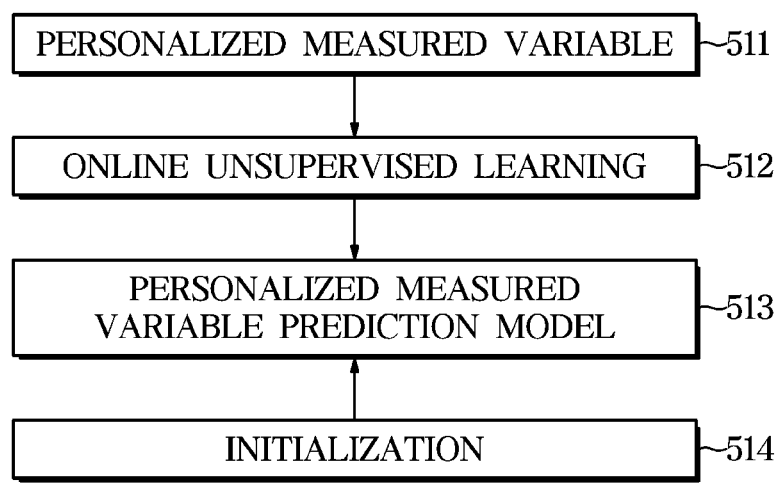
FIG. 5A is a flowchart of a process of performing personalization of an observation variable according to an embodiment.

FIG. 5A is flowchart of a process of performing personalization of an observation variable according to an embodiment.

Figure 5B:
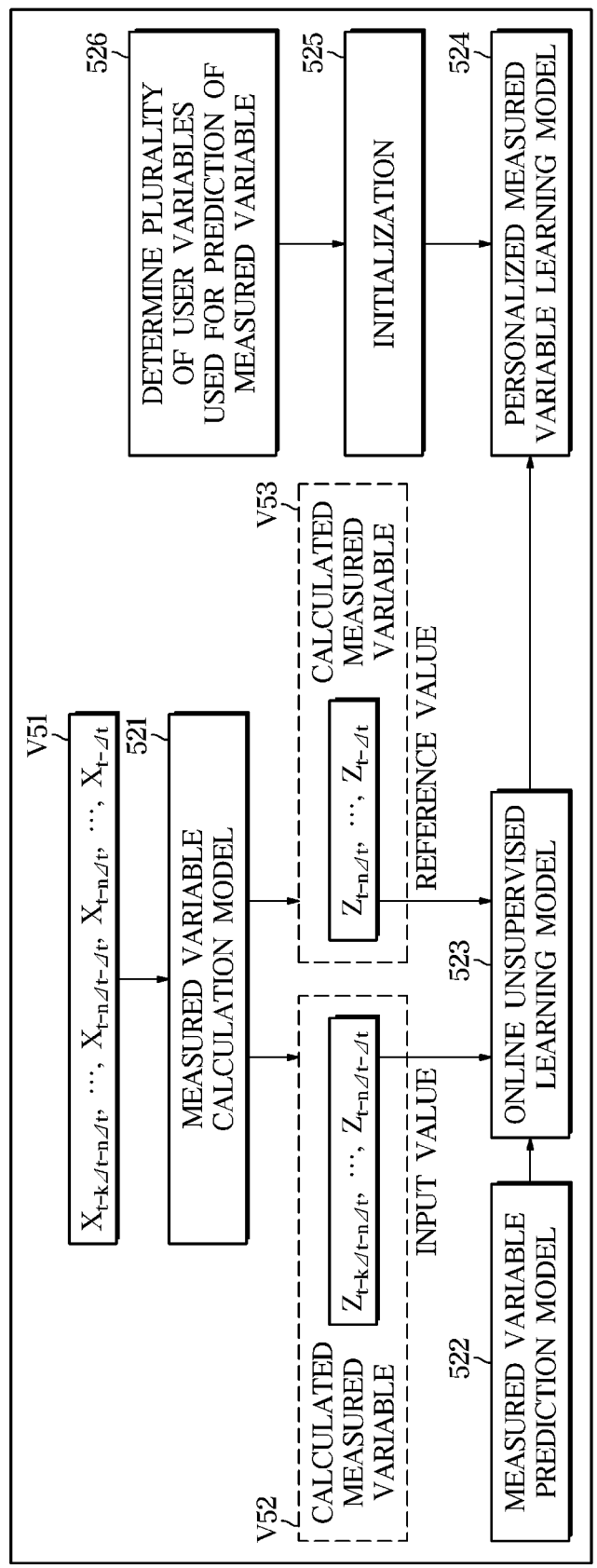
FIG. 5B is a diagram showing a process of performing the personalization described in FIG. 5A according to an embodiment.

FIG. 5B is diagram of the process of of performing the personalization described in FIG. 5A.

Referring to FIG. 5A, the processor may use the user measured variable (511) to perform the unsupervised learning (512) to predict a user measured variable on the basis of the learned data (513).

The personalized measured variable may be determined by performing the unsupervised learning on the basis of the predicted user measured variable and the plurality of other user measured variables (512).

The processor may predict the latent variable of the user on the basis of the learned data by performing the supervised learning on the basis of the personalized measured variable (513).

That is, step by step, the processor may perform unsupervised learning online on the basis of the personalized measured variable.

On the basis of this, the processor may predict the measured variable personalized for each user.

The processor may repeat this operation through initialization (514).

Specifically, referring to FIG. 5B, the processor may calculate the measured variable through a measured variable calculation model based on a measured variable V51 (V52).

The processor may perform the unsupervised learning with a part of the acquired measured variable as an input value V52 and another part as a reference value V53.

That is, the processor may determine the personalized measured variable by performing the unsupervised learning on the basis of the measured variable of the user corresponding to the first time point and the measured variable of the user corresponding to the second time point (523).

The processor may use a result of the measured variable prediction model in performing the online unsupervised learning (522).

The processor may perform online unsupervised learning to predict a personalized measured variable (524).

The processor may determine a plurality of user variables used for prediction of the observable variable and the processor may be continuously initialized to repeat the above-described operation (525).

A user variable used to predict the measured variable may be used to initialize the operation of the processor (526).

A model for predicting the personalized measured variable described in FIGS. 5A and 5B is an example embodiment, and the operation of the processor for predicting the personalized measured variable is not limited thereto.

Figure 6A:
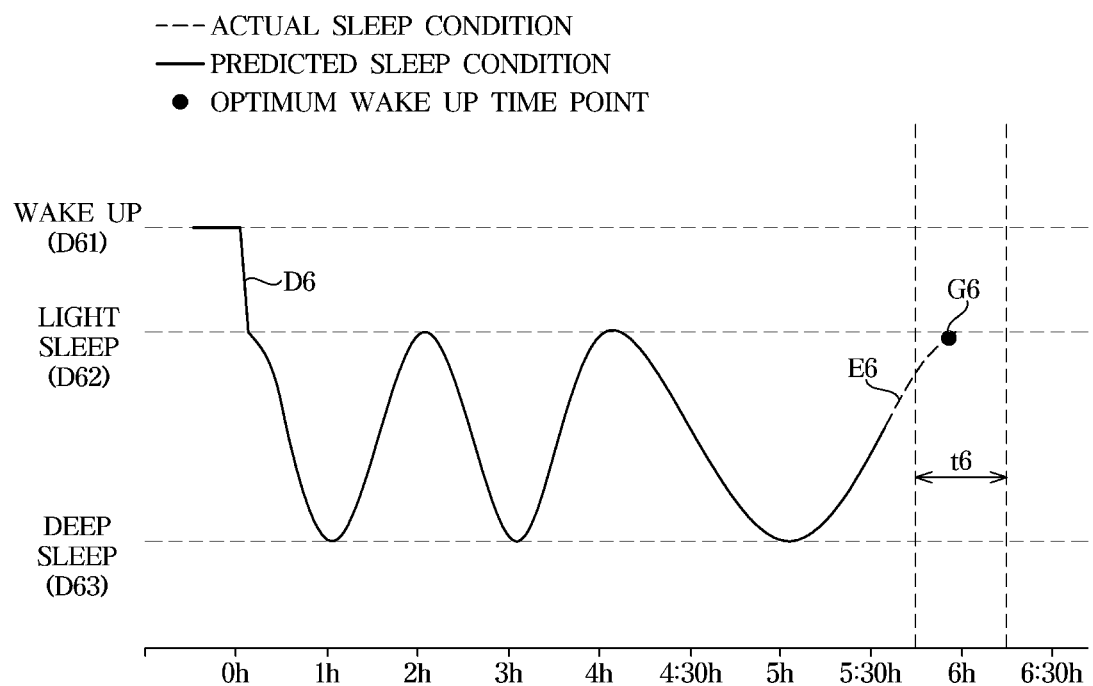
FIG. 6A is a graph for describing a measured variable and a latent variable in a user's sleep situation according to an embodiment.
Figure 6B:
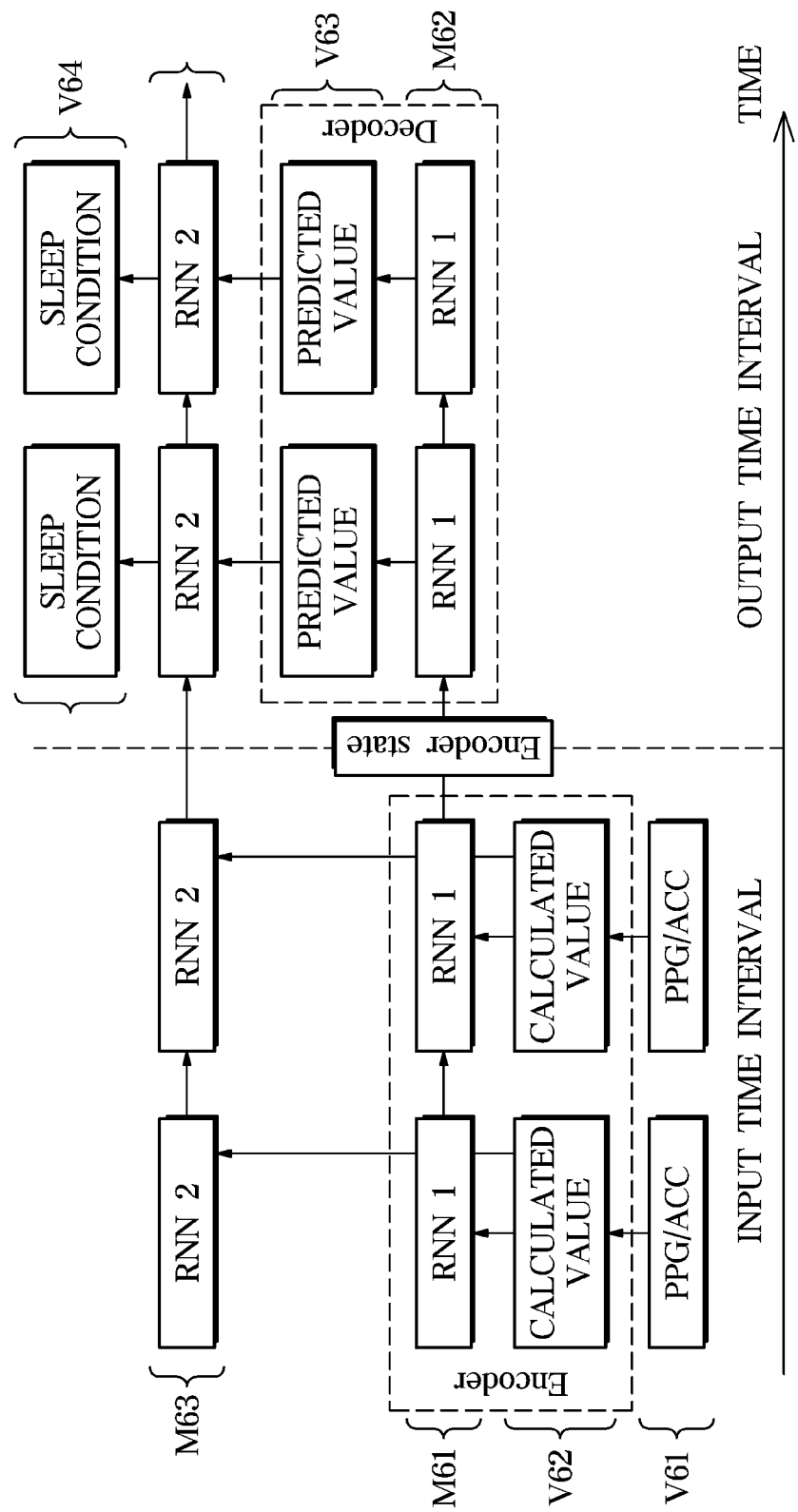
FIG. 6B is a diagram showing the overall modeling which performs an operation in FIG. 6A according to an embodiment.

FIG. 6A is a graph for describing the measured variable and the latent variable in a user's sleep situation according to an embodiment, and FIG. 6B is a diagram of the operation in FIG. 6A.

FIG. 6A is a graph showing contents related to a smart sleep alarm according to an embodiment.

Generally, human sleep is composed of deep sleep D63 during sleep, and may be represented as light sleep D62 when a human wakes up.

A time range shown in FIG. 6A may represent a user's desired wake-up time range (t6).

A solid line portion D6 represents a user's current sleep condition, and a dotted line portion E6 represents a user's sleep condition predicted by the above-described supervised and unsupervised models.

A point G6 may represent a sleep condition with the shallowest depth of sleep in the predicted sleep condition, that is, the sleep condition closest to a wake-up condition.

The sleep condition shown in FIG. 6A corresponds to the above-described latent variable, and hereinafter, an operation in which the processor predicts a sleep condition of a human as the latent variable will be described in detail.

As described above, the user's sleep condition may be the latent variable, and may be predicted through a method of predicting the measured variable and the latent variable using different learning modeling. This operation may be performed through FIG. 6B.

Referring to FIG. 6B, a prediction model of the sleep stage, in which latent variables V64 and V63, may be classified into predictive recurrent neural network 1 (RNN 1) models M61 and M62 of measurable variables V61 and V62 which may be calculated, and a RNN 2 model M63 for predicting the sleep stage, which is the latent variable.

That is, the RNN 1 models M61 and M62 may perform prediction of a calculable value, and the RNN 2 model M63 may perform estimation of a specified value of the labeling data.

Specifically, only photoplethysmogram (PPG) and accelerometer (ACC) data acquired by the sensor module without the labeling data are required for the data set for learning the RNN 1 models M61 and M62, and the RNN 1 models M61 and M62 may be personalized.

An operation of the RNN 1 and an operation of the RNN 2 will be separately described later.

Figure 7A:
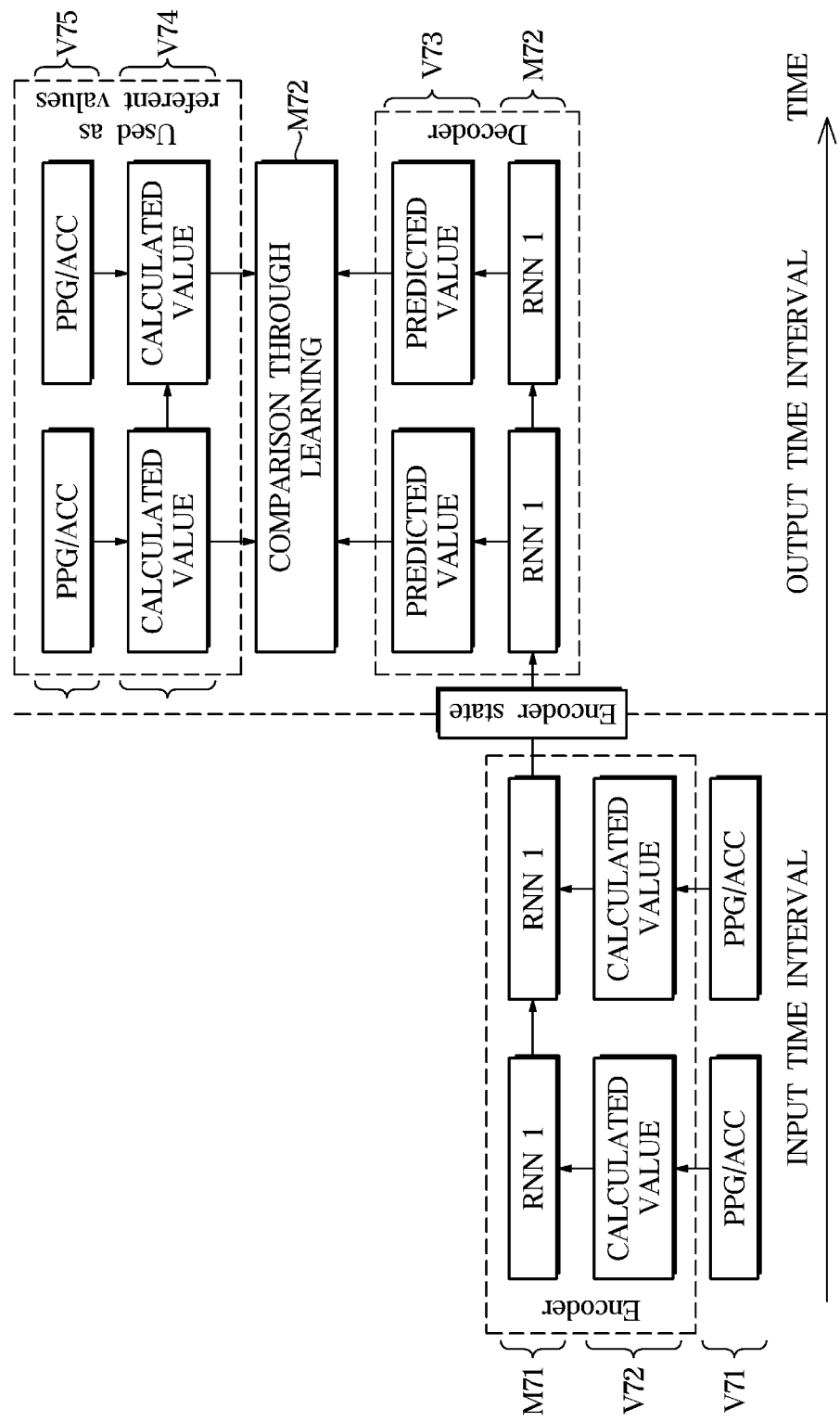
FIG. 7A is a diagram of a process of predicting the measured variable in the user's sleep situation according to an embodiment.

FIG. 7A is a diagram of a process of predicting the measured variable in the user's sleep situation according to an embodiment.

Referring to FIG. 7A, in a sleep condition of a human, measured variables V71 and V75 may be determined by PPG and ACC signals.

The latent variable and a predicted value may be determined as the sleep stage shown in FIG. 6A.

The sleep stage is a value calculated and predicted based on this input value rather than a value directly calculated from the PPG and ACC signals, and may be determined as the latent variable.

According to a embodiment, the measured variable prediction model may be formed based on an encoder-decoder long short-term memory model (LSTM).

Referring to FIG. 7A, when the electronic device acquires the PPG and ACC signals through the sensor, some signals may be determined as input values and some signals may be determined as reference values.

That is, some PPG and ACC signals may be encoded in the RNN 1 models through calculation and transmitted to other RNN 1 models M71 and M72.

Here, the unsupervised learning may be performed on the values determined as the reference values among the calculated PPG and ACC values and the acquired PPG and ACC values to predict PPG and ACC values, which are subsequent measured (M72).

The processor may perform an operation based on actual data, and may perform an operation without medical labeling data through the process disclosed in FIG. 7A.

Further, the model presented in FIG. 7A may derive the personalized measured variable by directly performing the above-described personalization online for a specific user.

Figure 7B:
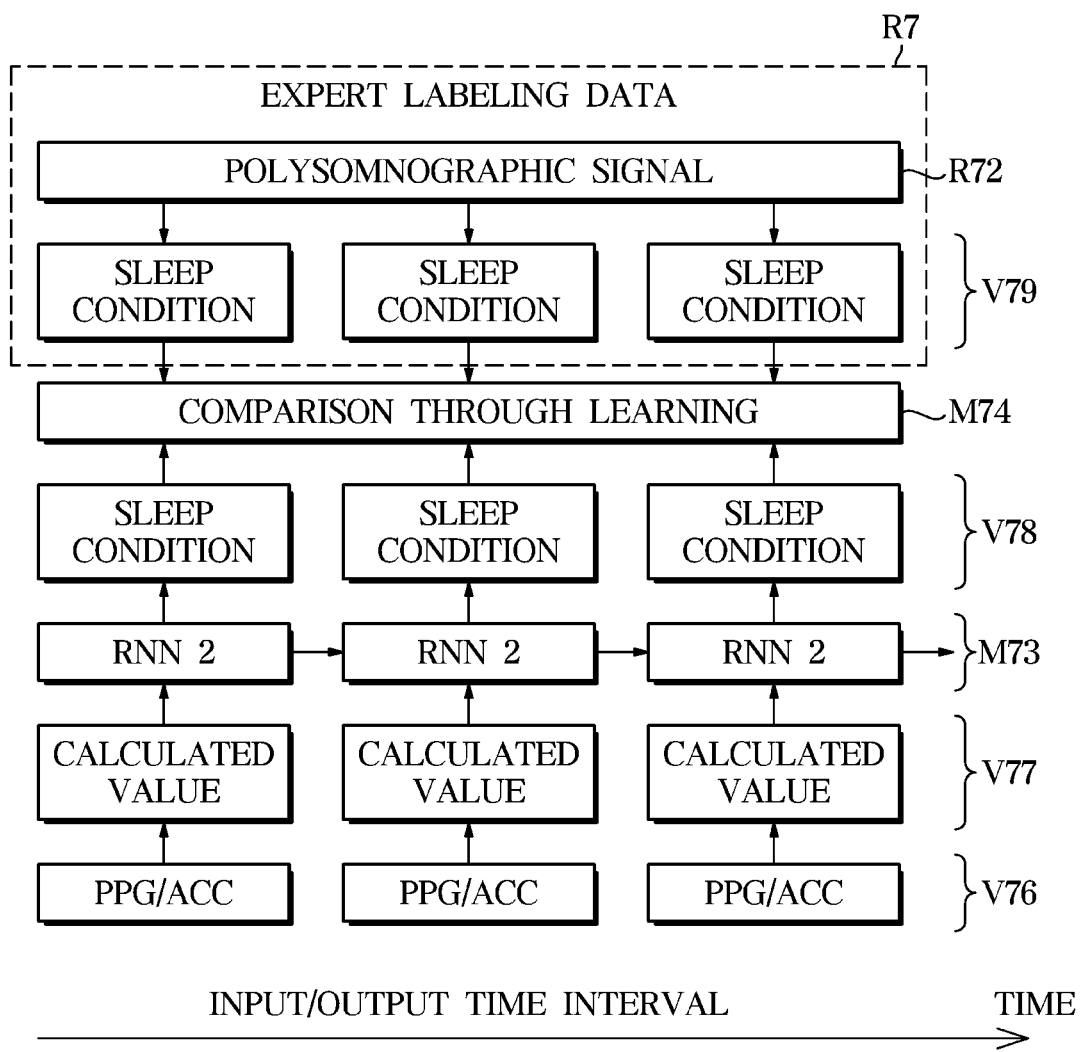
FIG. 7B is a diagram of a process of predicting the latent variable in the user's sleep situation according to an embodiment.

FIG. 7B is a diagram showing a process of predicting the latent variable in the user's sleep situation according to an embodiment.

FIG. 7B shows a model for predicting a latent variable different from that in FIG. 7A, and the supervised learning may be performed.

Accordingly, separate labeling data R7 is required in FIG. 7B.

FIG. 7B shows an operation using polysomnography data R72 as labeling data.

Polysomnography is a test for finding out a cause of a disorder which occurs during patient's sleep, and the processor may use the data acquired from these tests as the labeling data.

In polysomnography, electroencephalography, electrocardiography, electrooculography, electromyography, and video recording may be mainly performed.

That is, referring to FIG. 7B, data V79 for the sleep condition may be extracted from labeling data R7 and R72, and the supervised learning may be performed based on the PPG and ACC data calculated in FIG. 7A (V76 and V77).

Through this learning method, the processor may predict a latent variable for a sleep condition V78 (M74).

In the modeling presented in FIG. 7B, a bidirectional network may be applied, and a deep network may be applied.

Further, since a learning process in the modeling presented in FIG. 7B is direct, a deeper model may be trained without a prediction operation.

The processor may predict the latent variable, that is, the sleep condition based on the above-described operation to appropriately perform an operation to be described later for the user.

The above-described modeling is merely an embodiment, and there is no limitation on the form and implementation method of modeling.

Figure 8A:
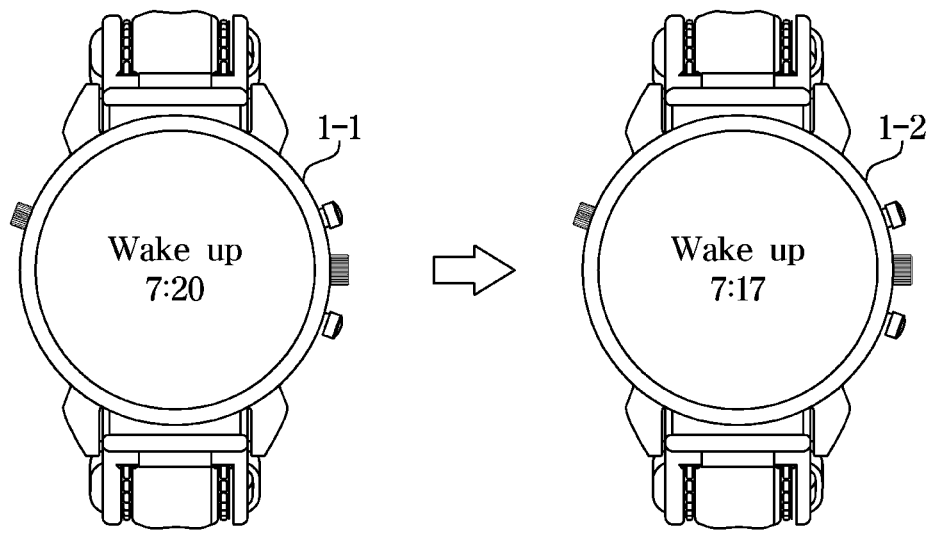
FIGS. 8A and 8B are diagram for describing a case in which a processor differently operates according to prediction of the latent variable in the user's sleep situation according to an embodiment.
Figure 8B:
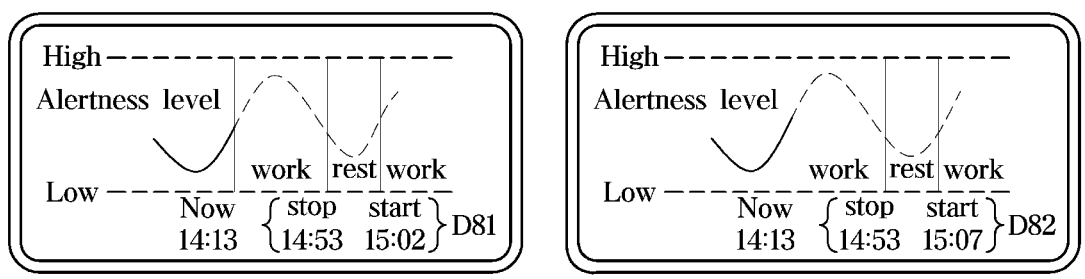

FIGS. 8A and 8B are diagrams for describing a case in which the processor operates differently according to the prediction of the latent variable in the user's sleep situation according to an embodiment.

Referring to FIG. 8A, the processor indicates that electronic devices 1-1 and 1-2 provide an alarm suitable for the user through the prediction of the latent variable based on sleep condition data acquired from the sensor.

FIG. 8A shows the electronic devices 1-1 and 1-2 as smart watches.

An operation of changing the output of a lamp to 7:17 on the basis of a physiological signal acquired by the sensor module when the user sets an alarm output time to 7:20 is described. Further, in this case, the electronic device 1-2 may determine that an alarm output time range is five minutes.

When the user inputs a wake-up alarm time as 7:20, the electronic devices 1-1 and 1-2 may determine to change the time for outputting the alarm at 7:20 by about five minutes.

That is, the processor may determine the alarm time output range on the basis of a command of the user. In this case, in a situation in which the electronic device 1-2 predicts the sleep condition of the user as entering deep sleep at 7:20, the lamp is turned on at 7:17 before proceeding to the deep sleep to induce wake up of the user.

The user may provide an alarm suitable for the user without being uniform through the model for predicting the above-described latent variable.

FIG. 8B show an operation of changing the alarm according to a physical condition of the user.

That is, in a normal situation, a rest time of the user may be determined as 14:53 to 15:02 (D81).

When a physical signal of the user is changed due to caffeine intake through coffee, smoking, drinking, and the like, the processor may differently predict the latent variable on the basis of the biometric signal of the user changed on the basis of the corresponding signal.

Accordingly, the processor may perform prediction by changing the end of the existing break time from 15:02 to 15:07 (D82).

The processor may predict a change of the latent variable of the user and the alarm time point presented in FIG. 8A may be changed to be suitable for the user on the basis of the above.

The operations disclosed in FIGS. 8A and 8B are merely one embodiment of the prediction of the latent variable, and does not limit the processor predicting the latent variable and performing the operations suitable for the user.

Figure 9:
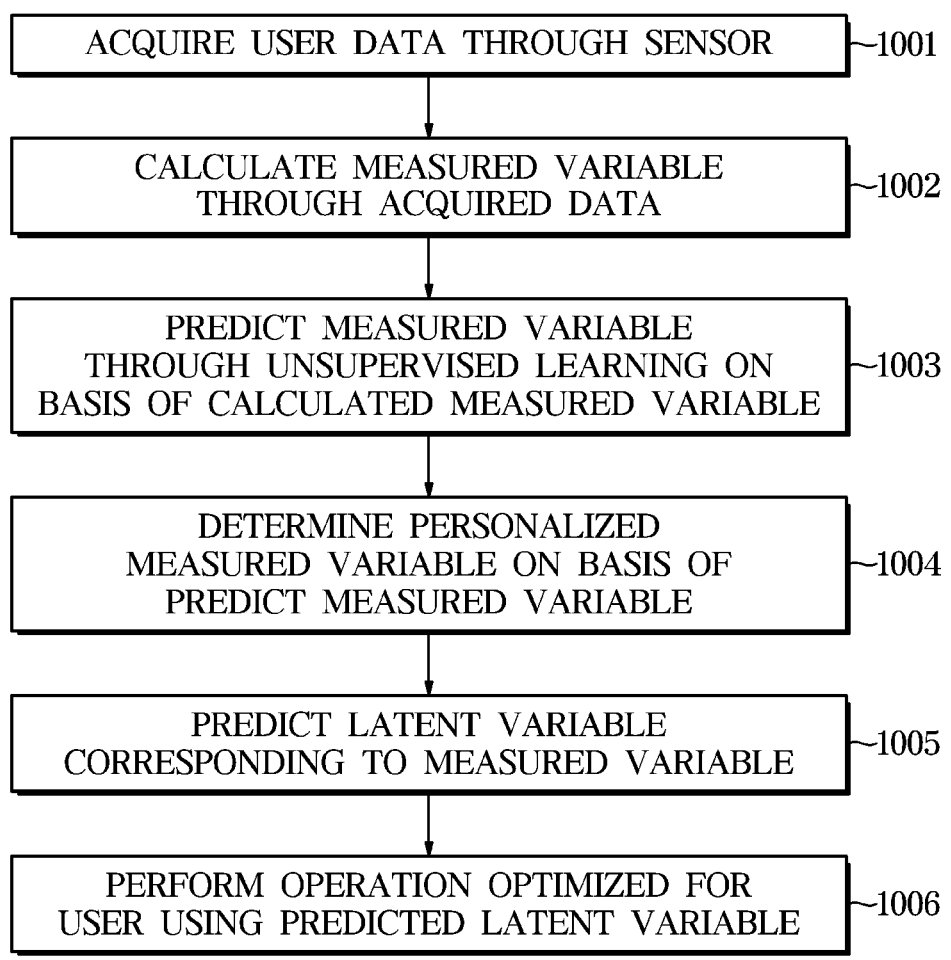
FIG. 9 is a flow chart of an operation of the electronic device according to an embodiment.

FIG. 9 is a flow chart for describing an operation of the electronic device according to an embodiment.

Referring to FIG. 9, the electronic device may acquire the user data through the sensor (1001).

The processor may calculate the measured variable based on the acquired data (1002).

The processor may classify the calculated measured variable into the input value and the reference value and perform the unsupervised learning to predict the measured variable (1003).

Further, the processor may determine the measured variable personalized for the user in this process (1004).

The processor may then predict the latent variable with the labeling data (1005).

Further, the electronic device may perform an operation of the electronic device optimized for the user using this predicted latent variable (1006).

The disclosed embodiments may be implemented in the form of a recording medium configured to store instructions executable by a computer. The instructions may be stored in a form of program code, and may generate program modules to perform the operations of the disclosed embodiments when executed by the processor. The recording medium may be implemented as a computer-readable recording medium.

The computer-readable recording medium may include any type of recording medium in which instructions readable by the computer are stored. For example, the recording medium may include a read only memory (ROM), a random-access memory (RAM), a magnetic tape, a magnetic disk, a flash memory, an optical data storage device, and the like.

An electronic device according to an embodiment and a method of controlling the same can use different models to predict a latent variable and a measured variable to predict a latent variable optimized for a user.

As described above, the disclosed embodiments have been described with reference to the accompanying drawings. Those skilled in the art should understand that the present disclosure may be performed differently from the disclosed embodiments without changing the technical spirit or essential features of the present disclosure. The disclosed embodiments are exemplary and should not be limitedly interpreted.

What is claimed is:

1. An electronic device comprising:
   a sensor configured to acquire a biometric signal of a user;
   a memory configured to store a measured variable of the user; and
   a processor configured to:
      receive biometric data of a plurality of other users and labeling data corresponding to the biometric data of the plurality of other users, wherein the labeling data comprises reference data related to medical diagnoses of measured physiological characteristics;
      predict, using an unsupervised learning model, biometric data of the user based on the biometric signal of the user;
      predict, using a supervised learning model, a biometric condition of the user based on the biometric data of the user, which is predicted by the unsupervised learning model, the biometric data of the plurality of other users, and the labeling data;
      obtain other predicted biometric data of the user, using the supervised learning model, based on the biometric data of the user and the labeling data: and
      obtain a personalized biometric data based on the predicted biometric data of the user and the biometric data of the plurality of other users,
   wherein the biometric signal of the user corresponds to a sleep characteristic of the user,
   wherein the biometric data of the plurality of other users corresponds to sleep conditions of the plurality of other users, and
   wherein the biometric condition of the user corresponds to a sleep condition of the user.

2. The electronic device of claim 1, wherein:
   the biometric data is a measured variable; and
   the biometric condition is a latent variable.

3. The electronic device of claim 2, wherein the unsupervised learning model uses data output by the supervised learning model as feedback to predict the measured variable of the user.

4. The electronic device of claim 3, wherein the processor is further configured to operate the unsupervised learning model independently of the labeling data.

5. The electronic device of claim 2, wherein the processor is further configured to:
obtain a predicted measured variable of the user, using the unsupervised learning model, based on the measured variable of the user and learned data, and
predict the latent variable using the supervised learning model based on the personalized measured variable and the learned data.

6. The electronic device of claim 5, wherein the processor is further configured to obtain the personalized measured variable based on a measured variable of the user corresponding to a first time point and a measured variable of the user corresponding to a second time point.

7. The electronic device of claim 2, wherein the processor is further configured to obtain a plurality of user variables for predicting the measured variable of the user and the latent variable of the user based on the measured variables of a predetermined physiological characteristic of the plurality of other users and the labeling data corresponding to the measured variables of the plurality of other users.

8. The electronic device of claim 1, further comprising:
an output interface configured to provide an alarm to the user; and
an input interface configured to receive a command of the user,
wherein the processor is further configured to obtain an alarm time which outputs the alarm based on the command input by the user, and change an output time of the alarm on based on the predicted latent variable.

9. A method of controlling an electronic device, comprising:
acquiring a biometric signal of a user;
receiving biometric data of a plurality of other users and labeling data corresponding to the biometric data of the plurality of other users, wherein the labeling data comprises reference data related to medical diagnoses of measured physiological characteristics;
predicting, using an unsupervised learning model, biometric data of the user based on the biometric signal of the user;
predicting, using a supervised learning model, a biometric condition of the user based on the biometric data of the user, which is predicted by the unsupervised learning model, the biometric data of the plurality of other users, and the labeling data;
obtaining other predicted biometric data of the user, using the supervised learning model, based on the biometric data of the user and the labeling data, and
obtaining a personalized biometric data based on the predicted biometric data of the user and the biometric data of the plurality of other users,
wherein the biometric data is a measured variable of the user, which is used by the unsupervised learning model, and the biometric condition is a latent variable of the user, which is used by the supervised learning model,
wherein the biometric signal of the user corresponds to a sleep characteristic of the user,
wherein the biometric data of the plurality of other users corresponds to sleep conditions of the plurality of other users, and
wherein the biometric condition of the user corresponds to a sleep condition of the user.

10. The method of claim 9, wherein the predicting of the measured variable comprises using data output by the supervised learning model as feedback.

11. The method of claim 10, wherein the predicting of the measured variable of the user comprises operating the unsupervised learning model independently of the labeling data.

12. The method of claim 9, wherein the predicting of the latent variable of the user, using the unsupervised learning model, comprises obtaining a predicted measured variable of the user based on the measured variable of the user and learned data, and
wherein the latent variable of the user is predicted using the supervised learning model based on the personalized measured variable and the learned data.

13. The method of claim 12, wherein the obtaining the personalized measured variable comprises obtaining the personalized measured variable of the user using the unsupervised learning model based on the measured variable of the user corresponding to a first time point and the measured variable of the user corresponding to a second time point.

14. The method of claim 9, further comprising obtaining a plurality of user variables based on measured variables of a predetermined physiological characteristic of the plurality of other users and the labeling data corresponding to the measured variables of the plurality of other users,
wherein predicting the measured variable of the user and the latent variable of the user is based on the measured variables of the predetermined physiological characteristic of the plurality of other users and the labeling data corresponding to the measured variables of the plurality of other users.

15. The method of claim 9, further comprising:
obtaining a time to output an alarm based on a command input by the user; and
changing the time to output the alarm on based on the predicted biometric condition.

16. An electronic device comprising:
an input interface configured to receive an alarm time from a user;
an output interface configured to output an alarm to the user;
a sensor configured to acquire a biometric signal of the user corresponding to a sleep characteristic, the biometrical signal comprising a photoplethysmogram (PPG) and accelerometer (ACC) data;
a memory configured to store the biometric signal of the user corresponding to the sleep characteristic; and
a processor configured to:
receive labeling data comprising biometric data of the sleep characteristic of a plurality of other users and polysomnography data corresponding to the biometric data of the plurality of other users;
predict biometric data of the user based on the biometric signal of the user using an unsupervised learning model; and
predict a sleep condition of the user based on the predicted biometric data of the user, the biometric data of the plurality of other users, and the labeling data.

17. The electronic device of claim 16, wherein the processor is further configured to obtain an alarm time output range based on an alarm time input by the user, and change the alarm time in the alarm time output range based on the predicted sleep condition.

18. The electronic device of claim 17, wherein the sensor comprises at least one of a photoplethysmography device, a gyro sensor, a blood oxygen measurement sensor, an electrocardiogram sensor, a bioimpedance sensor, or a temperature sensor.

* * * * *